United States Patent [19]

Bradford et al.

[11] Patent Number: Plant 7,050

[45] Date of Patent: Oct. 24, 1989

[54] NECTARINE TREE (DIAMOND JEWEL)

[76] Inventors: Norman G. Bradford, 11875 E. Savana Rd.; Lowell G. Bradford, 12439 E. Savana Rd., both of Le Grand, Calif. 95333

[21] Appl. No.: 283,820

[22] Filed: Dec. 12, 1988

[51] Int. Cl.[4] ..... A01H 5/00

[52] U.S. Cl. ..... Plt./41

[58] Field of Search ..... Plt./41

[56] References Cited

U.S. PATENT DOCUMENTS

P.P. 5,454 4/1985 Bradford ..... Plt. 41

*Primary Examiner*—James R. Feyrer

[57] ABSTRACT

The present invention relates to a nectarine tree and more particularly to a new and distinct variety broadly characterized by a medium size, medium vigor, hardy, very productive and regular bearing tree. The fruit matures under the ecological conditions described approximately the first week in June, with first picking on June 6, 1988, making it an early ripening variety, especially for a clingstone nectarine. The fruit is uniformly large in size, clingstone in type, very firm making excellent quality for keeping and shipping, full dark red in skin color, and acidic but sweet in flavor. The variety was developed as a hybridized seedling from the selected seed parent, Red Diamond (U.S. Plant Pat. No. 3,165), and an unnamed nectarine seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Diamond Jewel". The present variety was hybridized in 1983 by us in a cultivated area of our experimental orchard at Bradford Farms near Le Grand, Calif. in Merced County (San Joaquin Valley). It was the result of a seedling using Red Diamond (U.S. Plant Pat. No. 3,165) as the selected seed parent and an unnamed seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety most nearly resembles the fruit of May Diamond (U.S. Plant Pat. No. 5,454) by being a full red colored nectarine, by ripening in early June, and by having excellent firmness, but is distinguished therefrom and an improvement thereon by being a clingstone instead of a freestone and by being sweeter in flavor. Being a clingstone variety is becoming more desirable to the long distant shipper due to the absence of a pit cavity where internal breakdown often occurs. Also, improvements in flavor are very valuable in today's marketplace.

The present variety is similar to its selected seed parent, Red Diamond (U.S. Plant Pat. No. 3,165), in fruit appearance by being a full red colored nectarine with excellent firmness, but is distinguished therefrom by ripening 22 days earlier and by being a clingstone instead of a freestone.

DRAWING

The accompanying photograph shows the characteristics of the whole fruit in skin color and form, a characteristic fruit divided near its suture plane showing the flesh and pit cavity, a typical stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of eating ripe on June 11, 1988. All major color code designations are by reference to the Inter-Society Color Council, National Bureau of Standards. Common color names are also used occasionally.

TREE

Size: Medium.
Vigor: Medium.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Color.*—Grayish reddish brown [46. gy.rBr].
- *Lenticels.*—Numerous. Color: Moderate brown [58. m.Br]. Average size: ¼" [6.096 mm.].

Branches:
- *Size.*—Medium.
- *Texture.*—Medium.
- *Color.*—1st year wood — Topside: Moderate pink [5. m.Pk] in sunlight. 1st year wood — Underside: Light yellow green [119. l.YG]. Older wood: Deep brown [56. deep Br.].
- *Lenticels.*—Few, very small.

Leaves:
- *Size.*—Large. Average length: 6.5" [165.1 mm.]. Average width: 1⅜" [39.93 mm.].
- *Thickness.*—Medium.
- *Form.*—Elliptical.
- *Apex.*—Acuminate.
- *Base.*—Acute.

*Surface.*—Smooth.

*Color.*—Dorsal surface: Moderate olive green [125. m.OlG]. Ventral surface: Moderate yellow green [120. m.YG].

*Margin.*—Finely serrate. p2 *Venation.*—Pinnately net veined.

*Petiole.*—Average length: ½" [12.70 mm.]. Average thickness: 1/16" [1.588 mm.].

*Glands.*—Numbers: 2 to 6 per leaf. Position: Some oppositely and some alternately positioned on petiole and base of blade. Size: Medium. Form: Reniform. Color: Light yellow green [119. l.YG].

*Stipules.*—Numerous. Average length: 3/16" [4.763 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Size.*—Small.

*Color.*—Moderate pink [5. m.Pk].

FRUIT

Maturity when described: Hard but eating ripe, June 11, 1988.

Date of first picking: June 6, 1988.

Date of last picking: June 16, 1988.

Size: Uniform, large.

*Average diameter axially.*—2¼" [57.15 mm].

*Average traversely in suture plane.*—2 3/16" [55.56 mm].

Form: Uniform, symmetrical, globose to slightly oblong.

*Longitudinal section form.*—Round, but slightly compressed at the stem end.

*Transverse section through diameter.*—Round.

Suture: A shallow depression extending from the base to beyond the apex with a slight depression on both sides of the pistil point.

Ventral surface: Rounded slightly.

Lips: Slightly unequal with more lipping toward the apex.

Cavity: Flaring, elongated in the suture plane, suture showing on one side.

Base: Slightly cuneate and somewhat truncate.

Apex: Depressed within the suture.

Pistil point: Apical, negligible in length.

Stem: Medium size.

*Average length.*—5/16" [7.938 mm.].

*Average width.*—⅛" [3.175 mm.].

Skin:

*Thickness.*—Medium.

*Texture.*—Medium.

*Tenacity.*—Tenacious to flesh.

*Tendency to crack.*—None observed as of yet.

*Color.*—Dark red [16. d.R] over the entire surface with some brilliant orange yellow [67. brill.OY] freckling near the apex.

Flesh:

*Color.*—Brilliant yellow [83. brill.Y] to the pit.

*Surface of the pit cavity.*—Free of streaking.

*Amygdalin.*—Scarce.

*Juice.*—Abundant, rich.

*Texture.*—Extremely firm, fine, crisp.

*Fibers.*—Abundant, fine, tender.

*Ripens.*—Evenly.

*Flavor.*—A tasteful blend of acid with an abundance of sugar.

*Aroma.*—Pronounced.

*Eating quality.*—Very best.

STONE

Type: Clingstone.

Form: Oval.

Base: Straight.

Apex: Acute.

Sides: Equal.

Surface: Irregularly furrowed near the apex and pitted toward the base.

Ridges: Jagged toward the apex.

Color: Light yellowish brown [76. l.yBr].

Pit wall: 3/16" [4.763 mm.] thick.

Tendency to split: Very slight.

Kernel:

*Form.*—Oval.

*Taste.*—Sweet.

*Viable.*—Yes.

*Average width.*—7/16" [11.11 mm.].

*Average length.*—⅝" [15.88 mm.].

Pellicle color: Pale yellow [89. p.Y].

Amygdalin: Scant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct early ripening variety of clingstone nectarine tree, substantially as illustrated and described, which most nearly resembles the May Diamond (U.S. Plant Pat. No. 5,454) nectarine variety by producing fruit that is full red in color, ripens in early June, and is very firm in texture, but is distinguished from and an improvement on that variety by having fruit that is clingstone instead of freestone and that is much sweeter in flavor, both being valuable assets in today's marketplace.

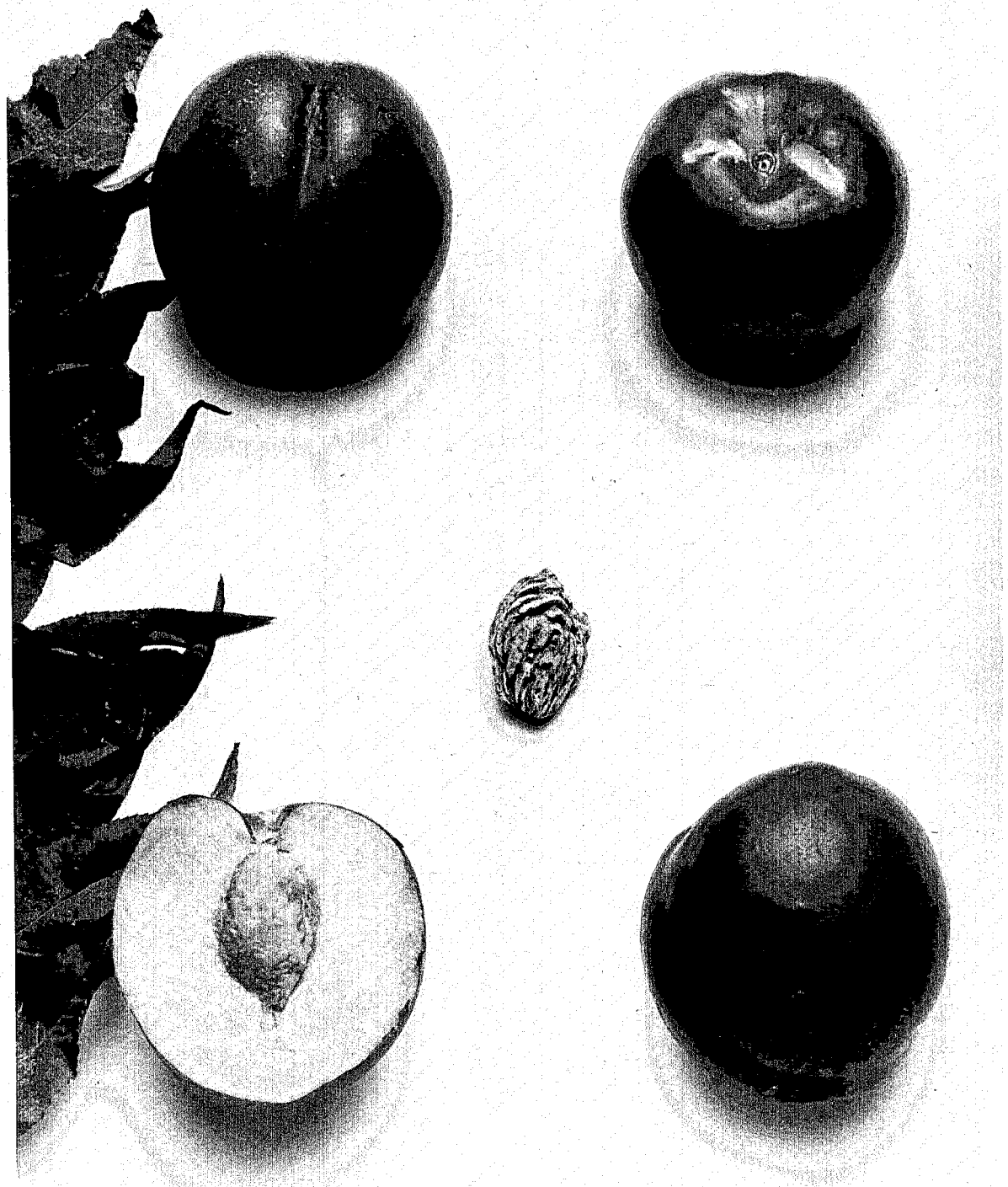

* * * * *